US012697095B2

(12) United States Patent
Imura et al.

(10) Patent No.:    US 12,697,095 B2
(45) Date of Patent:        Aug. 4, 2026

(54) SYSTEMS AND METHODS FOR INTRAVASCULAR VISUALIZATION

(71) Applicant: Boston Scientific Scimed, Inc., Maple Grove, MN (US)

(72) Inventors: Haruka Imura, Maple Grove, MN (US); Wenguang Li, Los Gatos, CA (US); Erik Stephen Freed, New Brighton, MN (US); Jennifer Gibbs, White Bear Lake, MN (US); Heather Drury, Dripping Springs, TX (US); Judith Tiferes Wang, Kenton, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 312 days.

(21) Appl. No.: 18/202,526

(22) Filed: May 26, 2023

(65) Prior Publication Data

US 2023/0380806 A1      Nov. 30, 2023

Related U.S. Application Data

(60) Provisional application No. 63/346,455, filed on May 27, 2022.

(51) Int. Cl.
A61B 8/00          (2006.01)
A61B 8/08          (2006.01)
G06T 7/00          (2017.01)

(52) U.S. Cl.
CPC ............ A61B 8/463 (2013.01); A61B 8/0891 (2013.01); G06T 7/0012 (2013.01); G06T 2207/10132 (2013.01); G06T 2207/30101 (2013.01)

(58) Field of Classification Search
None
See application file for complete search history.

(56)                  References Cited

U.S. PATENT DOCUMENTS 6,095,976 A  *  8/2000  Nachtomy .......... G01S 7/52046
                                                          600/443
6,945,938 B2     9/2005  Grunwald
                  (Continued)

FOREIGN PATENT DOCUMENTS

| CN | 112912011 A | 6/2021 |
| WO | 2021062006 A1 | 4/2021 |
| WO | 2021200985 A1 | 10/2021 |

OTHER PUBLICATIONS

International Search Report and Written Opinion dated Jul. 25, 2023 for International Application No. PCT/US2023/023667.

*Primary Examiner* — Mark R Milia
(74) *Attorney, Agent, or Firm* — Seager, Tufte & Wickhem, LLP

(57)                  ABSTRACT

Embodiments herein relate to intravascular imaging display systems and related methods. In an embodiment, an intravascular imaging display system is included having a control circuit and a video output circuit. The video output circuit can be configured to generate a display output including a user interface. The user interface can include graphical elements related to a vessel being imaged. The graphical elements can include a first detected feature portion at least partially defined by a first graphic indicator and a second detected feature portion at least partially defined by a second graphic indicator. The first graphic indicator can be visually distinct from the second graphic indicator. The first detected feature portion and the second detected feature portion can be assigned to represent one or more locations along a vessel wall by the control circuit based on a degree of attenuation of an ultrasound return signal crossing a threshold value.

20 Claims, 14 Drawing Sheets

(56) References Cited

U.S. PATENT DOCUMENTS

| 7,246,959 | B2 | 7/2007 | Nakatani |
| 7,306,561 | B2 | 12/2007 | Sathyanarayana |
| 2006/0100522 | A1 | 5/2006 | Yuan |
| 2006/0106320 | A1 | 5/2006 | Barbato |
| 2006/0173350 | A1 | 8/2006 | Yuan |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2020/0129142 | A1 | 4/2020 | Chao et al. |
| 2020/0129147 | A1* | 4/2020 | Nair ..................... A61B 8/469 |
| 2020/0129159 | A1* | 4/2020 | Rajguru ................ A61B 8/445 |
| 2020/0327664 | A1* | 10/2020 | Wilson ................ G06F 18/2431 |
| 2020/0359911 | A1* | 11/2020 | Olender ............... A61B 5/1076 |
| 2021/0090249 | A1 | 3/2021 | Choi et al. |

* cited by examiner

SYSTEMS AND METHODS FOR INTRAVASCULAR VISUALIZATION

CROSS-REFERENCE TO RELATED APPLICATIONS

This application claims the benefit of priority under 35 U.S.C. § 119 of U.S. Provisional Application No. 63/346,455, filed May 27, 2022, the entire disclosure of which is hereby incorporated by reference.

FIELD

Embodiments herein relate to intravascular imaging display systems and related methods.

BACKGROUND

Imaging systems such as intravascular ultrasound ("IVUS") imaging systems have been developed to provide a diagnostic tool for visualizing a variety of diseases or disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

SUMMARY

Embodiments herein relate to intravascular imaging display systems and related methods. In a first aspect, an intravascular imaging display system is included having a control circuit and a video output circuit. The video output circuit can be configured to generate a display output including a user interface. The user interface can include graphical elements related to a vessel being imaged. The graphical elements can include a first detected feature portion, wherein the first detected feature portion can be at least partially defined by a first graphic indicator. The graphical elements can include a second detected feature portion, wherein the second detected feature portion can be at least partially defined by a second graphic indicator. The first graphic indicator can be visually distinct from the second graphic indicator. The first detected feature portion and the second detected feature portion can be assigned to represent one or more locations along a vessel wall by the control circuit based on a degree of attenuation of an ultrasound return signal crossing a threshold value.

In a second aspect, in addition to one or more of the preceding or following aspects, or in the alternative to some aspects, the first graphic indicator can include a solid line border.

In a third aspect, in addition to one or more of the preceding or following aspects, or in the alternative to some aspects, the second graphic indicator can include an interrupted line border.

In a fourth aspect, in addition to one or more of the preceding or following aspects, or in the alternative to some aspects, the graphical elements can be related to a longitudinal cross-section of the vessel.

In a fifth aspect, in addition to one or more of the preceding or following aspects, or in the alternative to some aspects, the graphical elements can be related to a radial cross-section of the vessel.

In a sixth aspect, in addition to one or more of the preceding or following aspects, or in the alternative to some aspects, the first detected feature portion can include a representation of a first lumen border and a representation of a first vessel border. The second detected feature portion can include a representation of a second lumen border and a representation of a second vessel border.

In a seventh aspect, in addition to one or more of the preceding or following aspects, or in the alternative to some aspects, the position of the representations of the first vessel border, the second vessel border, the first lumen border, and the second lumen border can be determined using a machine learning derived model.

In an eighth aspect, in addition to one or more of the preceding or following aspects, or in the alternative to some aspects, the position of the representations of the first vessel border, the second vessel border, the first lumen border, and the second lumen border can be determined using a deep learning derived model.

In a ninth aspect, in addition to one or more of the preceding or following aspects, or in the alternative to some aspects, the user interface can include one or more numerical parameters related to the vessel being imaged, wherein the one or more numerical parameters include a typographic feature to indicate whether they relate to the first detected feature portion or the second detected feature portion.

In a tenth aspect, in addition to one or more of the preceding or following aspects, or in the alternative to some aspects, the user interface can be configured to receive user input regarding the position of the graphical elements from a system user.

In an eleventh aspect, in addition to one or more of the preceding or following aspects, or in the alternative to some aspects, the user interface can be configured to receive user input regarding at least one of a position of a representation of a first vessel border and a position of a representation of a second vessel border from a system user.

In a twelfth aspect, in addition to one or more of the preceding or following aspects, or in the alternative to some aspects, the intravascular imaging display system can be configured to use the user input as part of a data set for generation of a machine learning model.

In a thirteenth aspect, in addition to one or more of the preceding or following aspects, or in the alternative to some aspects, the first detected feature portion includes one or more discrete portions separated by one or more discrete portions of the second detected feature portion.

In a fourteenth aspect, a method of providing a display for an intravascular imaging display system can be included. The method can include distinguishing between a first vessel wall portion and a second vessel wall portion based on a degree of attenuation of an ultrasound return signal. The method can also include generating a display output including a user interface, wherein the user interface includes graphical elements related to a vessel being imaged including a first detected feature portion corresponding to the first vessel wall portion and a second detected feature portion corresponding to the second vessel wall portion. The first detected feature portion can be at least partially defined by a first graphic indicator and the second detected feature portion can be at least partially defined by a second graphic indicator. The first graphic indicator can be visually distinct from the second graphic indicator.

In a fifteenth aspect, in addition to one or more of the preceding or following aspects, or in the alternative to some aspects, the first graphic indicator can include a solid line border and the second graphic indicator can include an interrupted line border.

In a sixteenth aspect, in addition to one or more of the preceding or following aspects, or in the alternative to some aspects, the method can further include determining positions of the graphical elements related to a vessel being imaged using a machine learning derived model.

In a seventeenth aspect, in addition to one or more of the preceding or following aspects, or in the alternative to some aspects, the method can further include determining positions of the graphical elements related to a vessel being imaged using a deep learning derived model.

In an eighteenth aspect, in addition to one or more of the preceding or following aspects, or in the alternative to some aspects, the method can further include receiving user input regarding the graphical elements related to a vessel being imaged from a system user.

In a nineteenth aspect, in addition to one or more of the preceding or following aspects, or in the alternative to some aspects, the method can further include receiving user input regarding a position of a vessel border from a system user.

In a twentieth aspect, in addition to one or more of the preceding or following aspects, or in the alternative to some aspects, the method can further include using the user input as part of a training data set for generation of a machine learning model.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
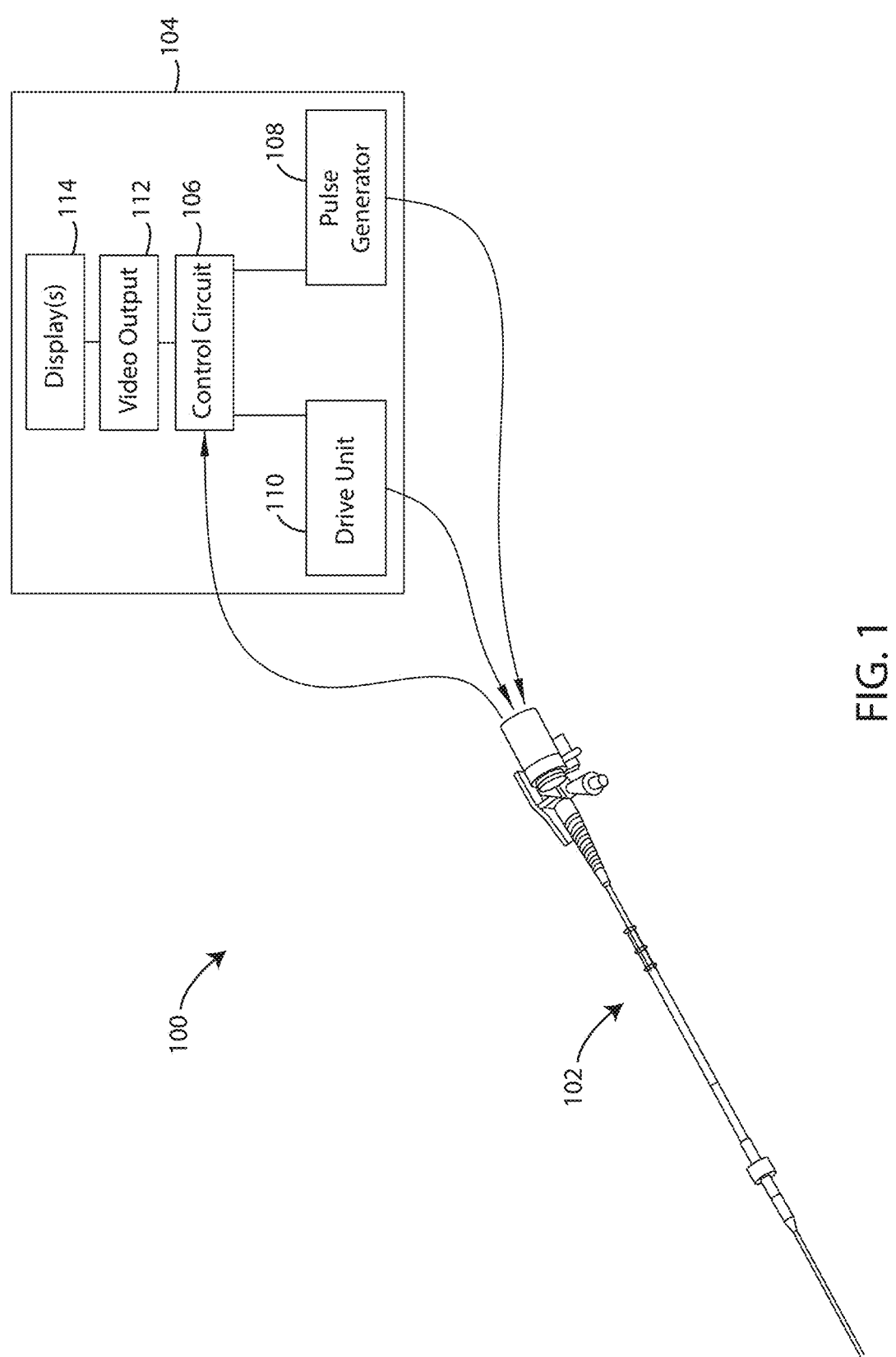
FIG. 1 is a schematic view of an intravascular imaging system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, imaging systems have been developed to provide a diagnostic tool for visualizing a variety of diseases or disorders. As an example, an IVUS imaging system can include a control module (with a pulse generator, an image processor, and a display or monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

The value of imaging systems can be enhanced by automatically identifying portions of the anatomy of clinical interest and/or automatically calculating measurements of the same. For example, in some scenarios the system can automatically determine the position of anatomical features of interest (such as a vessel lumen border and/or a vessel wall border) by evaluating the imaging signals using machine learning techniques. Specifically, a model can be generated through machine learning techniques (such as a supervised learning approach, a deep learning approach, and/or the like) and then applied to imaging signals to identify the position of anatomical features of interest and/or measurements of the same. The position of anatomical features of interest and/or measurements of the same can then be displayed within a user interface of a system herein in the form of displayed or drawn graphical elements indicative of anatomical features of interest and/or measurements or properties of the same.

However, in many cases, the ability to accurate determine the position of anatomical features of interest in an automated manner by the system is dependent on the ability to gather enough imaging signals with a sufficient signal to noise ratio. Some conditions (such as the presence of a plaque that attenuates ultrasound signals) can interfere with the imaging process and, specifically, attenuate signals gathered by the system and/or reduce the signal to noise ratio of the same to levels preventing the accurate and reliable identification of the position of anatomical features of interest in an automated way by the system. In such cases, while the system may still be able to estimate positions of such features, the estimations may lack a typical level of positional accuracy for the system. In such cases, it can be important for the system user (such as a clinician) to be cognizant of the positional accuracy of features drawn by the system, such as instances of possible reduced positional accuracy.

Embodiments herein can provide information to a system user, such as through a user interface, regarding the positional accuracy of identified positions of anatomical features of interest and/or measurements of the same. In various embodiments herein, an intravascular imaging display system can display graphical components in a manner that provides information about the positional accuracy of the same. For example, in various embodiments herein, an intravascular imaging display system can display graphical components related to a vessel wall including a first vessel wall portion at least partially defined by a first graphic indicator and a second vessel wall portion at least partially defined by a second graphic indicator that is visually distinct from the first graphic indicator. The first vessel wall portion and the second vessel wall portion can each represent one or more locations along a vessel wall exhibiting different degrees of positional accuracy or confidence as determined by the control circuit based on a degree of attenuation of an ultrasound return signal or based on another metric or approach. Thus, the visually distinct first vessel wall portion and the second vessel wall portion can be used to visually signal a difference in the accuracy of determining the position of the same to the system user.

In various embodiments, a method of providing a display for an intravascular imaging display system herein can include operations of distinguishing between a first vessel wall portion and a second vessel wall portion based on a degree of attenuation of an ultrasound return signal or another metric or approach (such as signal to noise ratio or the like) indicative of accuracy of position of anatomical features of interest and/or measurements of the same and generating a display output including a user interface. The user interface can include graphical components related to a representation of a vessel wall including a representation of the first vessel wall portion and a representation of the second vessel wall portion. The representation of the first vessel wall portion can be at least partially defined by a first graphic indicator and the representation of the second vessel wall portion can be at least partially defined by a second graphic indicator.

Referring now to FIG. 1, a schematic view of an intravascular imaging system 100 is shown in accordance with various embodiments herein. In this example, the intravascular imaging system 100 takes the form of an IVUS imaging system. However, other imaging systems are contemplated including optical coherence tomography imaging systems. The intravascular imaging system 100 includes a catheter 102 that is coupleable to a processing unit or control module 104. The control module 104 may include, for example, a control circuit 106, a pulse generator 108, a drive unit 110, a video output circuit 112, and one or more displays or display units 114. In some instances, the pulse generator 108 forms electric pulses that may be input to one or more transducers disposed in the catheter 102.

For the purposes herein, the term "display" may either refer to an electronic device (e.g., such as a monitor, etc.) used for the visual representation of data and/or to the visual representation of data itself. In other words, the term "display" may refer to a hardware device for displaying data as well as the data displayed on the hardware device, depending on the context.

In some instances, mechanical energy from the drive unit 110 may be used to drive an imaging core disposed in the catheter 102. In some instances, electric signals transmitted from the one or more transducers may be input to the control circuit 106 for processing. In some instances, the processed electric signals from the one or more transducers can be displayed as one or more images on the one or more display units 114. For example, a scan converter can be used to map scan line samples (e.g., radial scan line samples, or the like) to a two-dimensional Cartesian grid to display the one or more images on the one or more display units 114.

In some instances, the control circuit 106 may also be used to control the functioning of one or more of the other components of the control module 104. For example, the control circuit 106 may be used to control at least one of the frequency or duration of the electrical pulses transmitted from the pulse generator 108, the rotation rate of the imaging core by the drive unit 110, the velocity or length of the pullback of the imaging core by the drive unit 110, or one or more properties of one or more images formed on the one or more display units 114.

Figure 2:
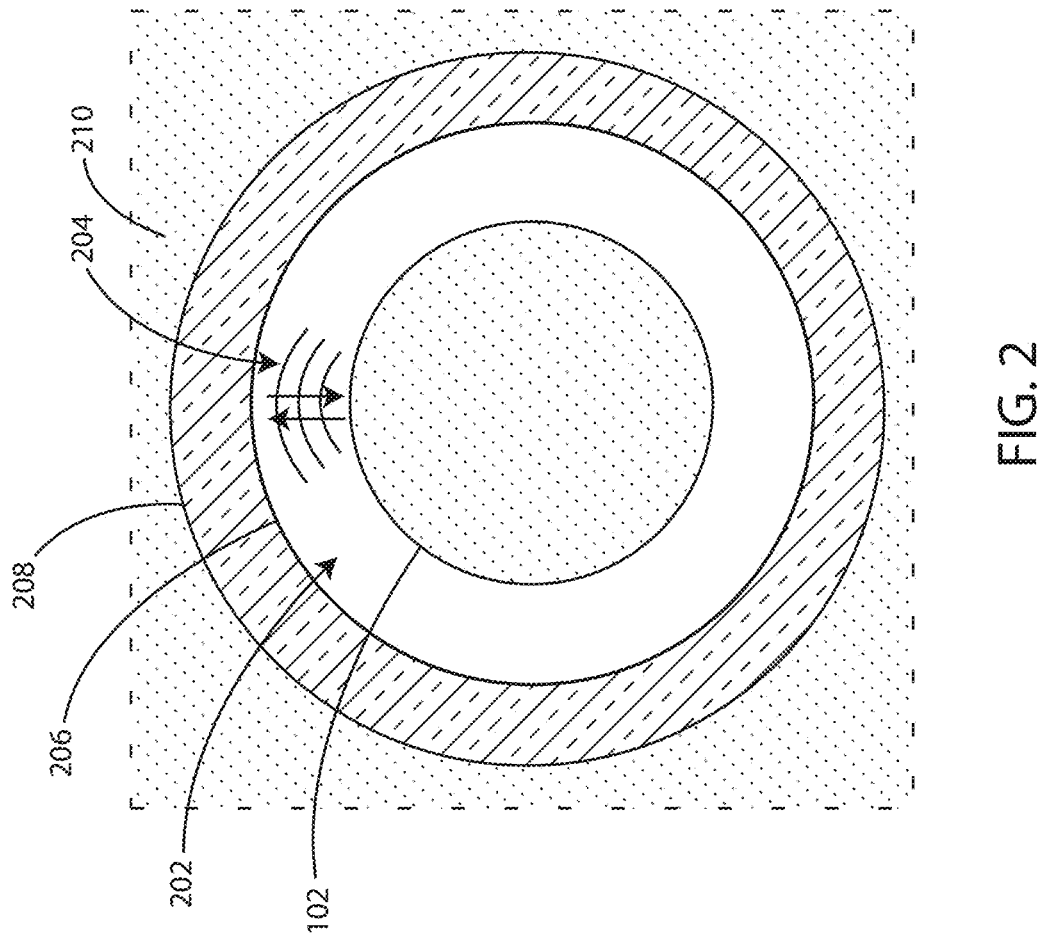
FIG. 2 is a radial cross-sectional view of a vessel being imaged in accordance with various embodiments herein.

Referring now to FIG. 2, a radial cross-sectional schematic view of a vessel being imaged is shown in accordance with various embodiments herein. FIG. 2 illustrates a catheter 102 and ultrasound acoustic pulses 204 coming from the same. The vessel being imaged includes a vessel lumen 202 and a lumen border 206. The vessel also includes a vessel border 208. FIG. 2 also shows a surrounding tissue 210. The ultrasound acoustic pulses 204 pulses are reflected by such portions of the tissue and are then processed by the system to generate images such as those shown in FIGS. 4-15.

Figure 3:
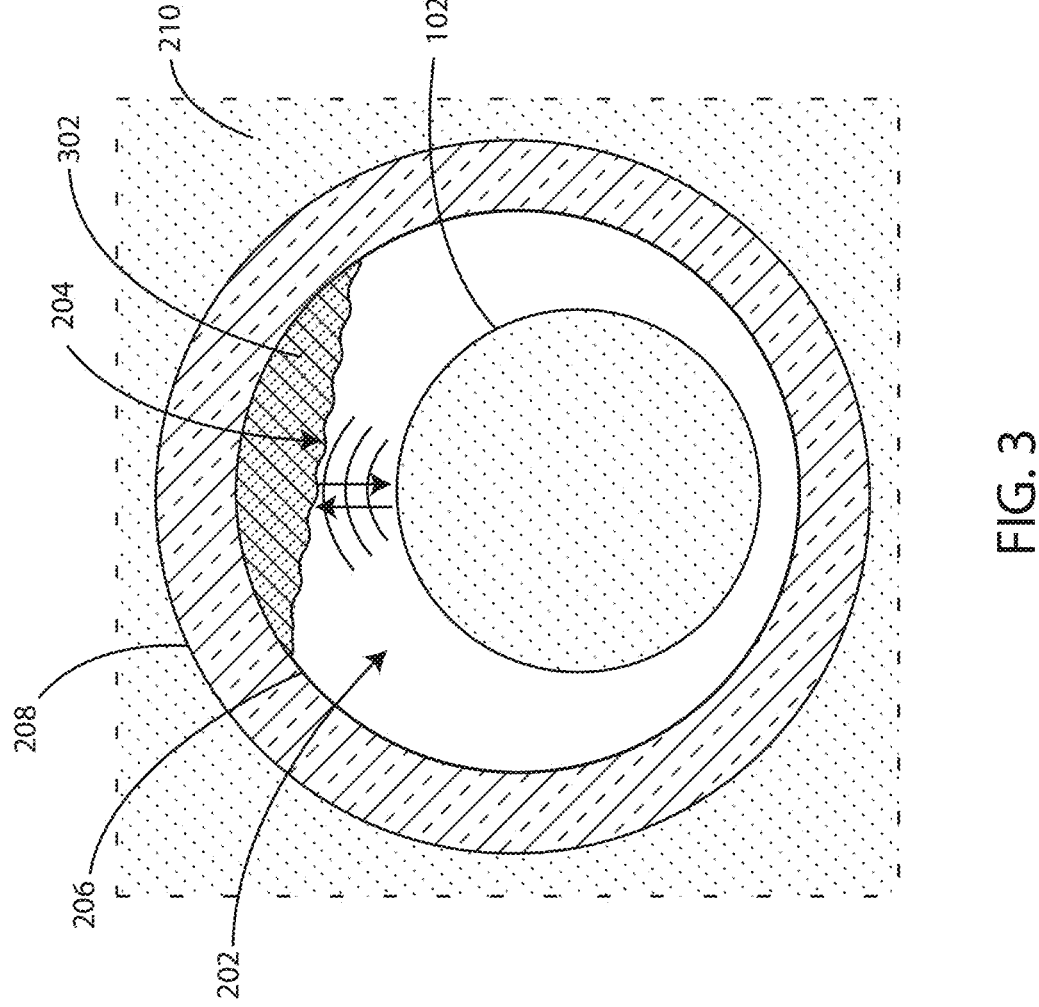
FIG. 3 is a radial cross-sectional view of a vessel being imaged in accordance with various embodiments herein.

However, plaques that attenuate ultrasound signals can interfere with ultrasound imaging by attenuating the amount of the signal reaching and/or reflecting back from anatomical features such as the vessel border. Referring now to FIG. 3, a radial cross-sectional schematic view of a vessel being imaged is shown in accordance with various embodiments herein. As with FIG. 2, FIG. 3 shows a catheter 102 and ultrasound acoustic pulses 204 coming from the same along with a vessel lumen 202, a lumen border 206, a vessel border 208, and surrounding tissue 210. However, in FIG. 3 a plaque 302 that attenuates ultrasound signals is also depicted. The plaque 302 can attenuate the ultrasound signal making automatic determinations of the locations of features such as the vessel border 208 less accurate.

Figure 4:
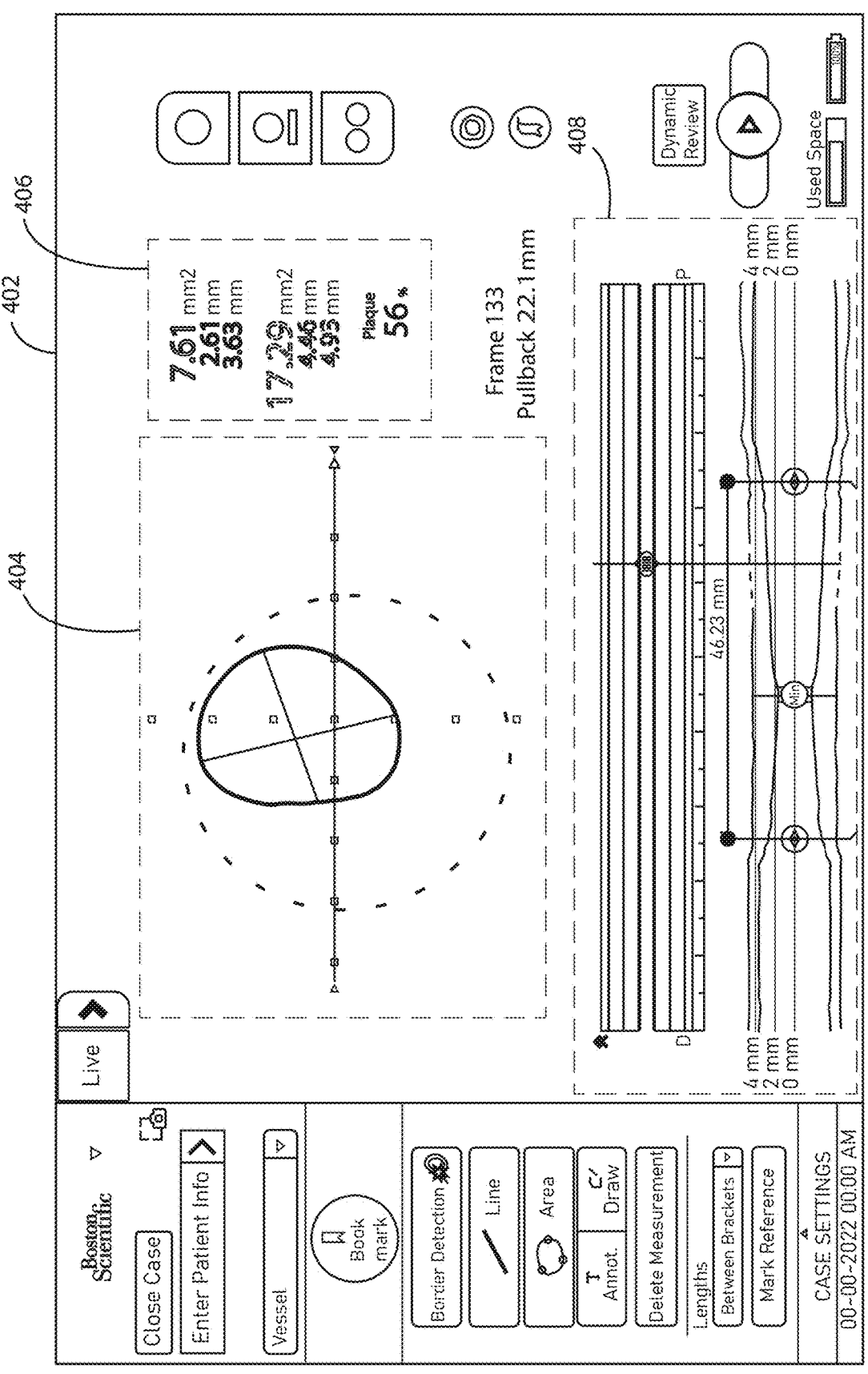
FIG. 4 is a schematic view of a display for an intravascular imaging system in accordance with various embodiments herein.

Embodiments of imaging systems herein can include a user interface wherein ultrasound images and/or representations of the same are shown including graphical elements indicating the location of anatomical features in a manner so that the positional accuracy of the location is visually apparent to the system user. Referring now to FIG. 4, a schematic view of a display 114 for an intravascular imaging system is shown in accordance with various embodiments herein. FIG. 4 shows a user interface 402. The user interface 402 includes features related to a radial cross section 404 of a vessel being imaged. The user interface 402 also includes a measurement parameter area 406. The user interface 402 also includes features related to a longitudinal cross section 408 of the vessel being imaged.

Figure 5:
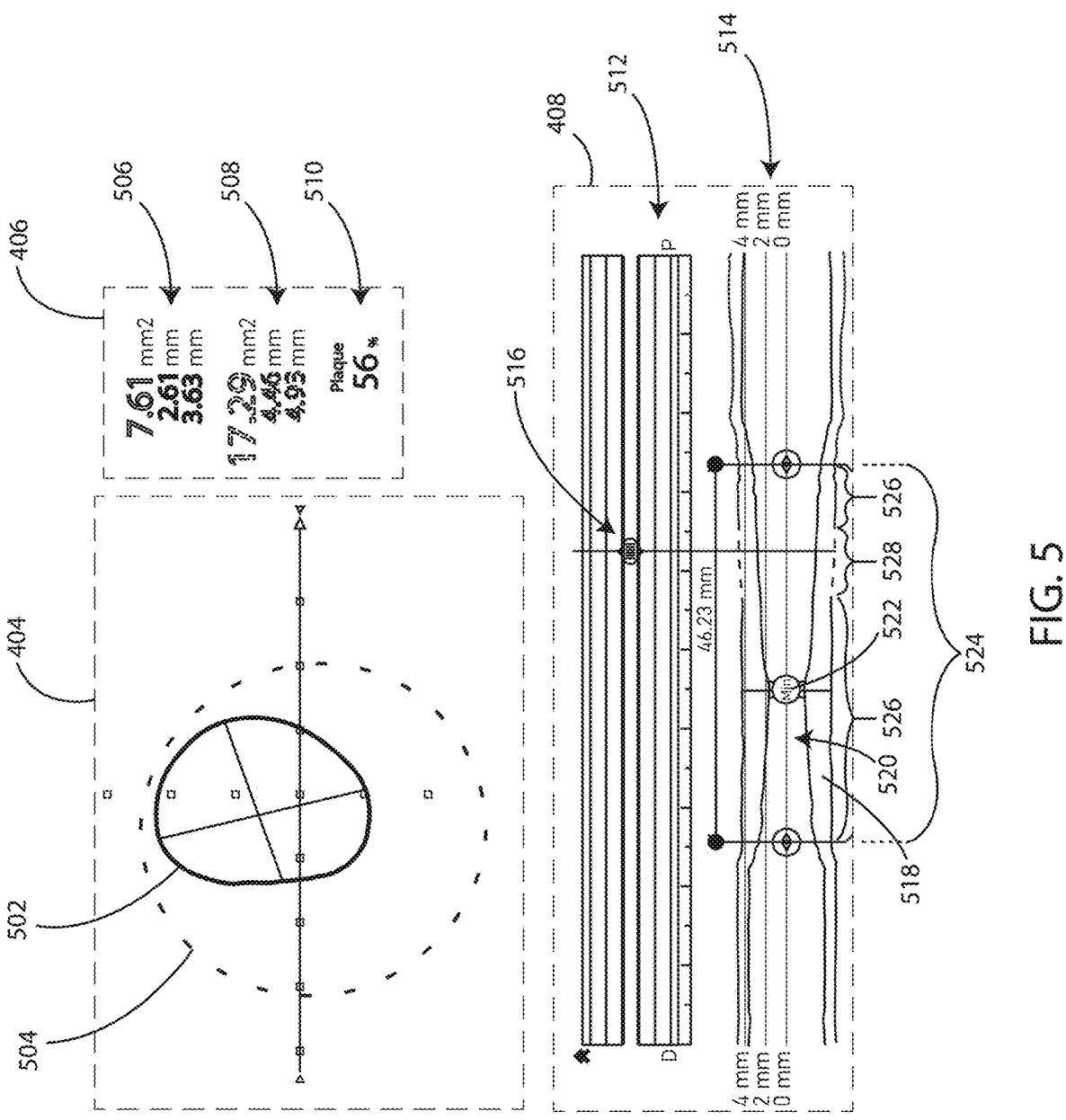
FIG. 5 is a schematic view of components of a display for an intravascular imaging system in accordance with various embodiments herein.

Referring now to FIG. 5, a schematic view of certain components of a display 114 for an intravascular imaging system is shown in accordance with various embodiments herein. The user interface includes features related to a radial cross section 404 of the vessel being imaged. In this example, the features related to the radial cross section 404 include a drawn lumen border 502 and a drawn vessel border 504. In this example, the drawn lumen border 502 is shown with a graphic indicator or graphical element in the form of a solid line while the drawn vessel border 504 is shown with a graphic indicator in the form of a dashed or broken line. This visual distinction in the lines can be used to indicate an area where signal attenuation (or another effect) may impact the accuracy of position of the drawn vessel border 504 as shown through the user interface. In contrast, when the drawn vessel border 504 is believed to be shown with high positional accuracy, then the drawn vessel border 504 can be shown in the user interface with a solid or unbroken line.

The user interface can also include a measurement parameter area 406. The measurement parameter area 406 can include various measurements such as lumen measurements 506, vessel measurements 508, plaque data 510, and the like. In this example, the lumen measurements 506 are shown in a font including solid lines while the vessel measurements 508 are shown in a font including dashed or broken lines. This can be used to indicate to a system user that the lumen measurements 506 are of a high degree of accuracy while the vessel measurements 508 may be less accurate due to signal attenuation or another effect at that portion of the vessel. Instead of, or in addition to, showing the data distinctly by using dashed lines versus solid lines, other visually distinguishing techniques (such as other typographical features) can be used such as showing measurements that may be less accurate in a different color, with a different typeface, in italics, bolded, underlined, with different kerning, with different fill, with a different border, or the like.

The user interface can also include graphical components related to a longitudinal cross section 408 of a vessel being imaged. In this example, the graphical components related to a longitudinal cross section 408 can include a distal to proximal navigation guide 512 as well as a navigation slider 516 that can be used by the system user to navigate quickly navigate through the image data longitudinally along the length of the imaged vessel.

The user interface can also include a longitudinal vessel wall representation 514. The longitudinal vessel wall representation 514 can include a focus area 524 with a lumen 520 and a vessel wall 518. The vessel wall 518 can include a first vessel wall portion 528 and a second vessel wall portion 526. The first vessel wall portion 528 includes a first lumen border 502. The first vessel wall portion 528 also includes a first vessel border 504. The user interface can also include a marker of the minimum cross-sectional area 522 of the lumen.

The first vessel wall portion 528 and the second vessel wall portion 526 can be assigned to represent one or more locations along a vessel wall 518 by a control circuit 106 based on a degree of attenuation of an ultrasound return signal crossing a threshold value. The first vessel wall portion 528 can be one continuous segment or can be divided into multiple discrete segments. Similarly, the second vessel wall portion 526 can one continuous segment or divided into multiple discrete segments. In various embodiments, the first vessel wall portion 528 can be divided up into multiple discrete portions separated by a second vessel wall portion 526. In various embodiments, the first vessel wall portion 528 can be at least partially defined by a first graphic indicator. In various embodiments, the first graphic indicator can include a solid line border. In various embodiments, the second vessel wall portion 526 can be at least partially defined by a second graphic indicator. In various embodiments, the second graphic indicator can include a dashed, broken, or otherwise interrupted line border.

In various embodiments, the system can use a threshold value of signal attenuation to distinguish what portions of the longitudinal vessel wall representation 514 are the first vessel wall portion 528 and what portions of the longitudinal vessel wall representation 514 are the second vessel wall portion 526. In some embodiments, the threshold value can be predetermined. In some embodiments, the threshold value can be dynamically set. The threshold value for a degree of attenuation can be predetermined or dynamically set. In some embodiments, the threshold value for a degree of signal attenuation can be 1, 2, 3, 5, 7, 10, 20, 30, 40, 50, 60, 70, 80, 90 percent attenuation or less or more, or a value falling within a range between any of the foregoing.

In various embodiments, positions of the first vessel border 504 and a second vessel border 208 are determined using a machine learning derived model. In various embodiments, the first vessel border 504 and a second vessel border 208 are determined using a deep learning derived model.

Figure 6:
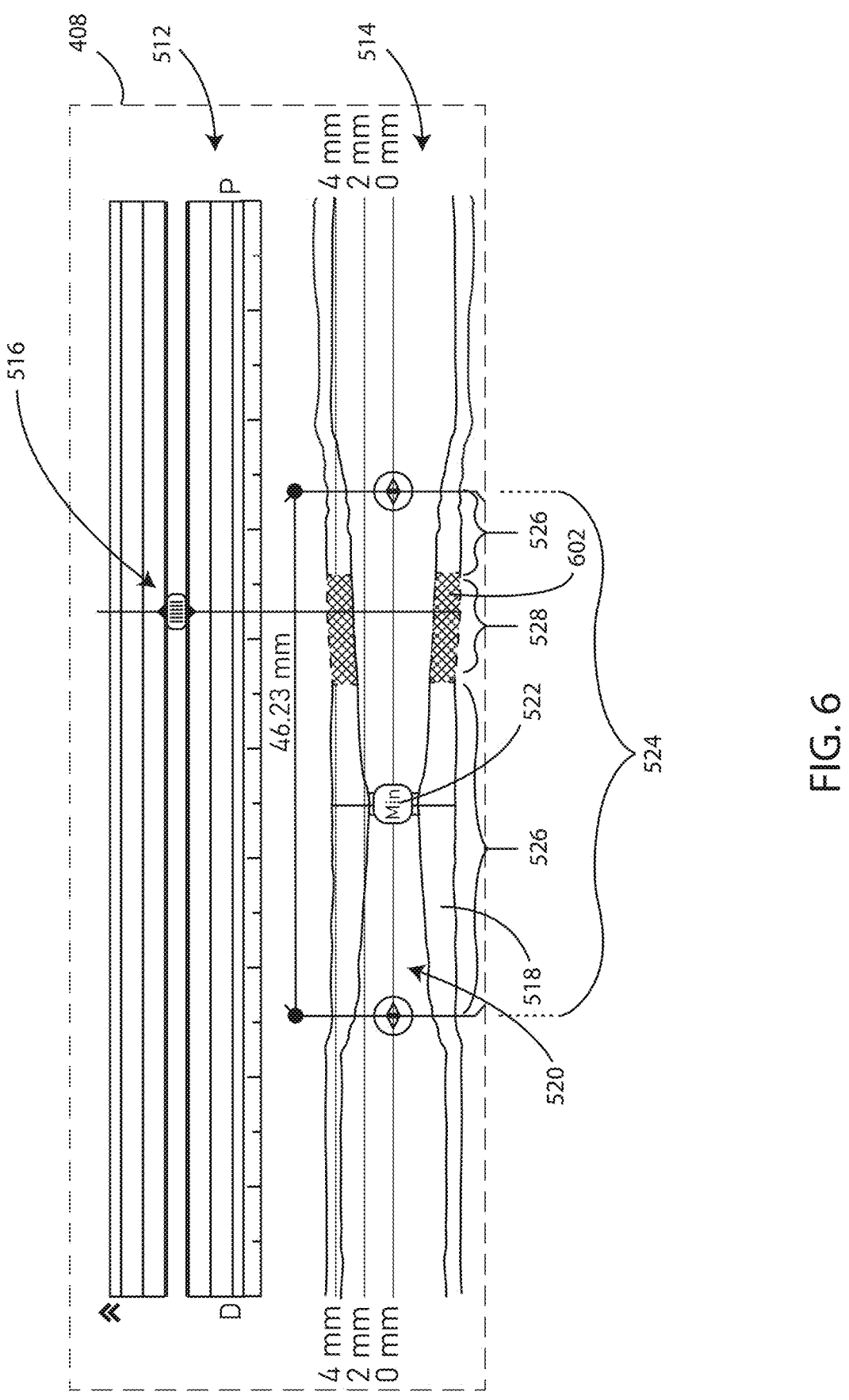
FIG. 6 is a schematic view of components of a display for an intravascular imaging system in accordance with various embodiments herein.

Many different techniques can be used to make the first vessel wall portion representation and the second vessel wall portion representation visually distinguishable from one another. Referring now to FIG. 6, a schematic view of components of a display for an intravascular imaging system is shown in accordance with various embodiments herein. FIG. 6 shows graphical components related to a longitudinal cross section 408 of the vessel being imaged. As in FIG. 5, the longitudinal cross section 408 includes a distal to proximal navigation guide 512, a navigation slider 516, and a longitudinal vessel wall representation 514. The longitudinal vessel wall representation 514 includes graphic elements representing the vessel wall 518, the vessel lumen 520, and a marker of the minimum cross-sectional area 522 of the lumen. The vessel wall can be divided up graphically into a first vessel wall portion 528 and a second vessel wall portion 526. In this embodiment, the vessel wall 518 includes a filled portion 602, which relates to the first vessel wall portion 528. The filled portion 602 can make the first vessel wall portion 528 even more visually distinct.

Figure 7:
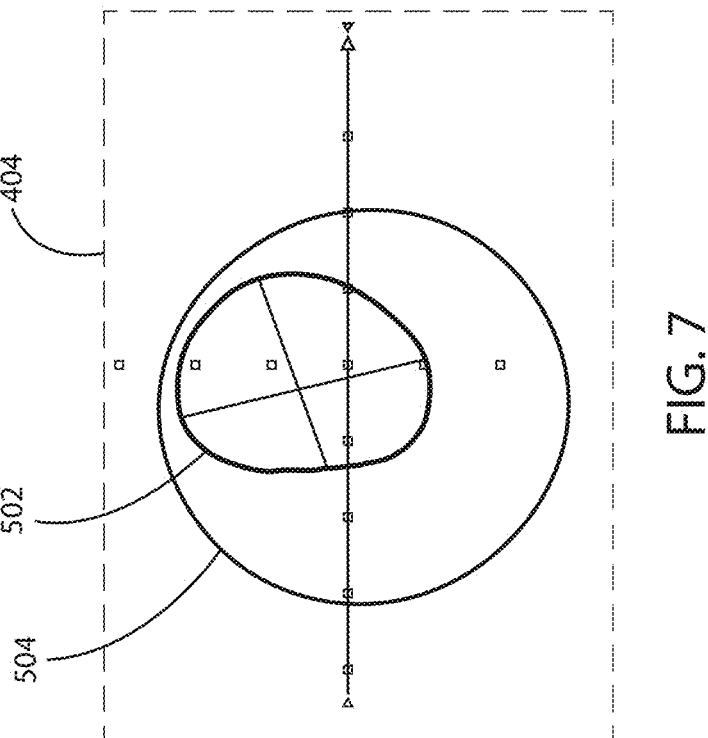
FIG. 7 is a schematic view of components of a display for an intravascular imaging system in accordance with various embodiments herein.

When the system user navigates to a portion of the vessel where signal attenuation is sufficiently low, then the drawn vessel border 504 can be illustrated with a solid line. Referring now to FIG. 7, a schematic view of components of a display for an intravascular imaging system is shown in accordance with various embodiments herein. The user interface includes features related to a radial cross section

404 of the vessel being imaged including a drawn lumen border 502 and a drawn vessel border 504. In this example, both of the drawn lumen border 502 and a drawn vessel border 504 are shown in solid lines.

Figure 8:
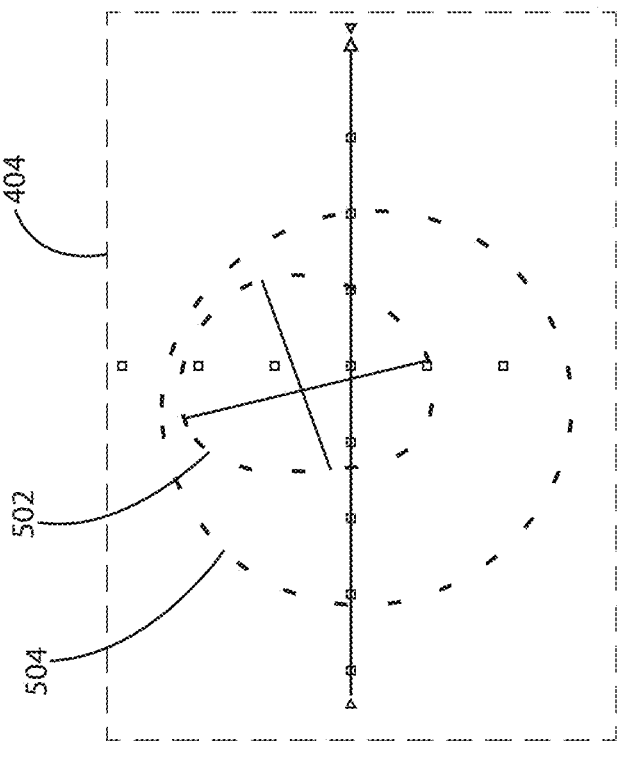
FIG. 8 is a schematic view of components of a display for an intravascular imaging system in accordance with various embodiments herein.

In some scenarios, positions of features other than just the vessel border can be displayed indicating a reduced confidence of positional accuracy. Referring now to FIG. 8, a schematic view of components of a display for an intravascular imaging system is shown in accordance with various embodiments herein. The user interface includes features related to a radial cross section 404 of the vessel being imaged including a drawn lumen border 502 and a drawn vessel border 504 wherein both of the drawn lumen border 502 and the drawn vessel border 504 are displayed with broken lines.

Figures 9, 10:
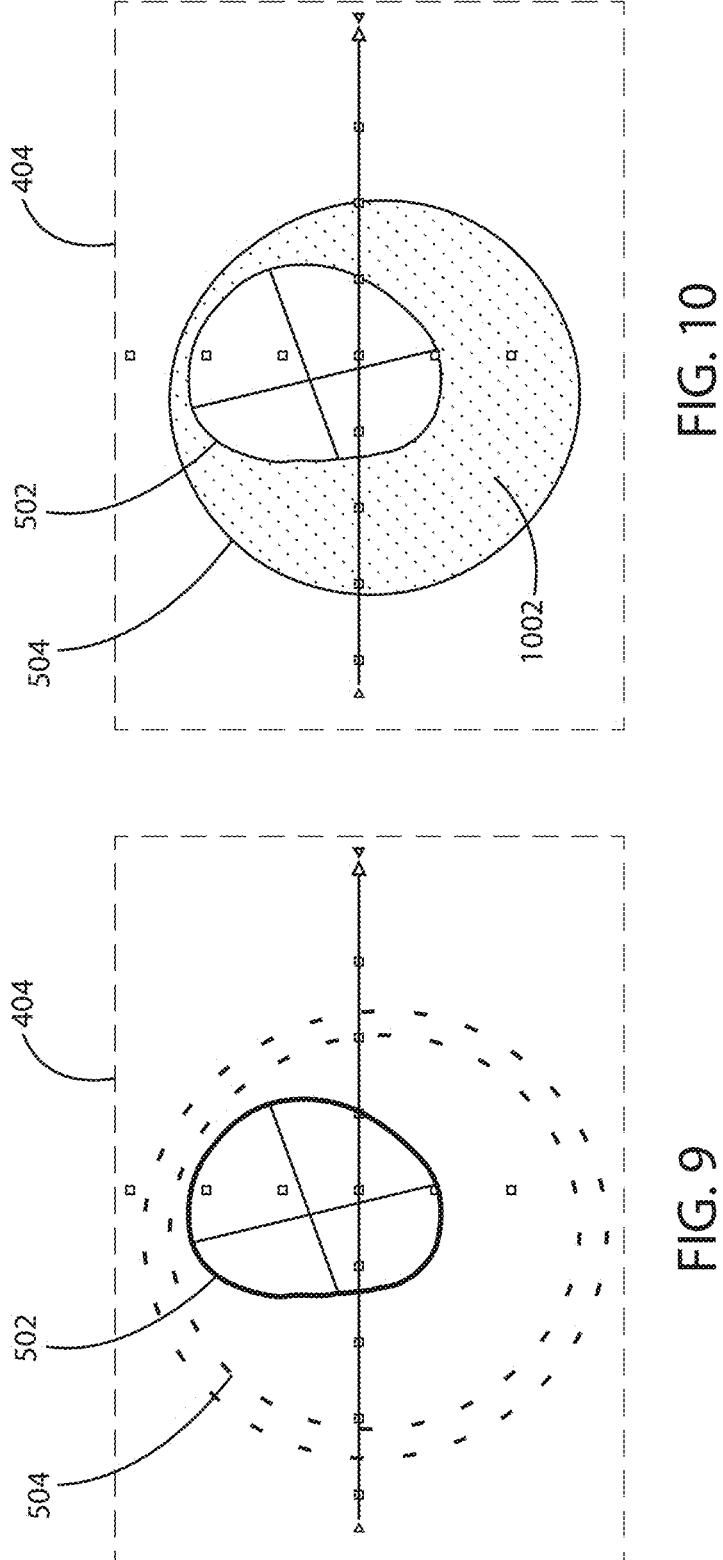
FIG. 9 is a schematic view of components of a display for an intravascular imaging system in accordance with various embodiments herein.
FIG. 10 is a schematic view of components of a display for an intravascular imaging system in accordance with various embodiments herein.

In some embodiments, multiple lines can be used to illustrate a reduced confidence of positional accuracy. Referring now to FIG. 9, a schematic view of components of a display for an intravascular imaging system is shown in accordance with various embodiments herein. The user interface includes features related to a radial cross section 404 of the vessel being imaged including a drawn lumen border 502 and a drawn vessel border 504. In this example, the drawn vessel border 504 is illustrated with double lines. However, triple lines or a different number of offset lines are also contemplated herein.

In some embodiments, one or more filled sections can be included with the user interface to illustrate a reduced confidence of positional accuracy. Referring now to FIG. 10, a schematic view of graphical components of a user interface of a display for an intravascular imaging system are shown in accordance with various embodiments herein. The user interface includes features related to a radial cross section 404 of the vessel being imaged including a drawn lumen border 502 and a drawn vessel border 504. The user interface can also include a filled section 1002 between the drawn lumen border 502 and the drawn vessel border 504.

Figures 11, 12:
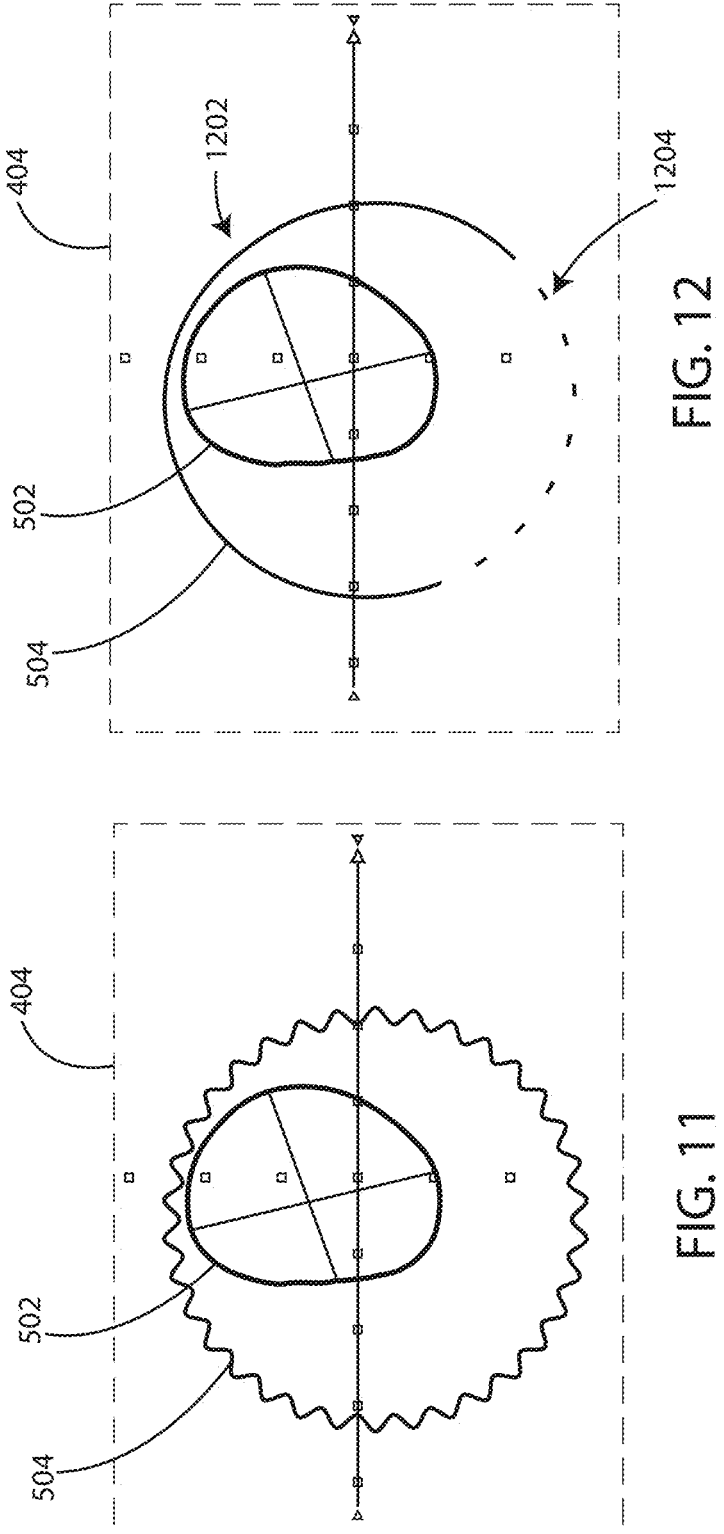
FIG. 11 is a schematic view of components of a display for an intravascular imaging system in accordance with various embodiments herein.
FIG. 12 is a schematic view of components of a display for an intravascular imaging system in accordance with various embodiments herein.

In some embodiments, an irregular line and/or a zig-zag line can be included with the user interface to illustrate a reduced confidence of positional accuracy. Referring now to FIG. 11, a schematic view of components of a display including a user interface for an intravascular imaging system is shown in accordance with various embodiments herein. The user interface includes features related to a radial cross section 404 of the vessel being imaged including a drawn lumen border 502 and a drawn vessel border 504. In this example, the drawn vessel border 504 is shown as a zig-zag line to visually indicate a reduced degree of confidence of positional accuracy.

In some embodiments, only a portion of the radial-cross section may be subject to a reduced degree of confidence of position accuracy. For example, perhaps a signal attenuating plaque does not wrap around the vessel 360 degrees. In such a scenario, it is possible that a specific radial portion of an anatomical feature of interest may be subject to a reduced degree of confidence of position accuracy, but the rest may not. As such, in some embodiments a portion of a graphic element such as a line may be displayed in one manner while the rest may be displayed differently. Referring now to FIG. 12, a schematic view of components of a display for an intravascular imaging system is shown in accordance with various embodiments herein. The user interface includes features related to a radial cross section 404 of the vessel being imaged including a drawn lumen border 502 and a drawn vessel border 504. In this example, the drawn vessel border 504 includes a portion 1202 as a solid line and another portion 1204 as a dashed or broken line.

In various embodiments herein, actual ultrasound images can be shown as part of the display. For example, in various embodiments herein at least some components of a display described herein can be overlayed on, superimposed over or near, or otherwise shown in conjunction with an ultrasound image such as a radial cross-sectional ultrasound image or a longitudinal cross-sectional ultrasound image. As a specific example, a drawn lumen border and/or a drawn vessel border can be overlayed on a radial cross-sectional ultrasound image. In this manner, a system user can simultaneously see the actual ultrasound image as well as where the system has determined the lumen border and the vessel border to be located (e.g., the drawn borders).

Figure 13:
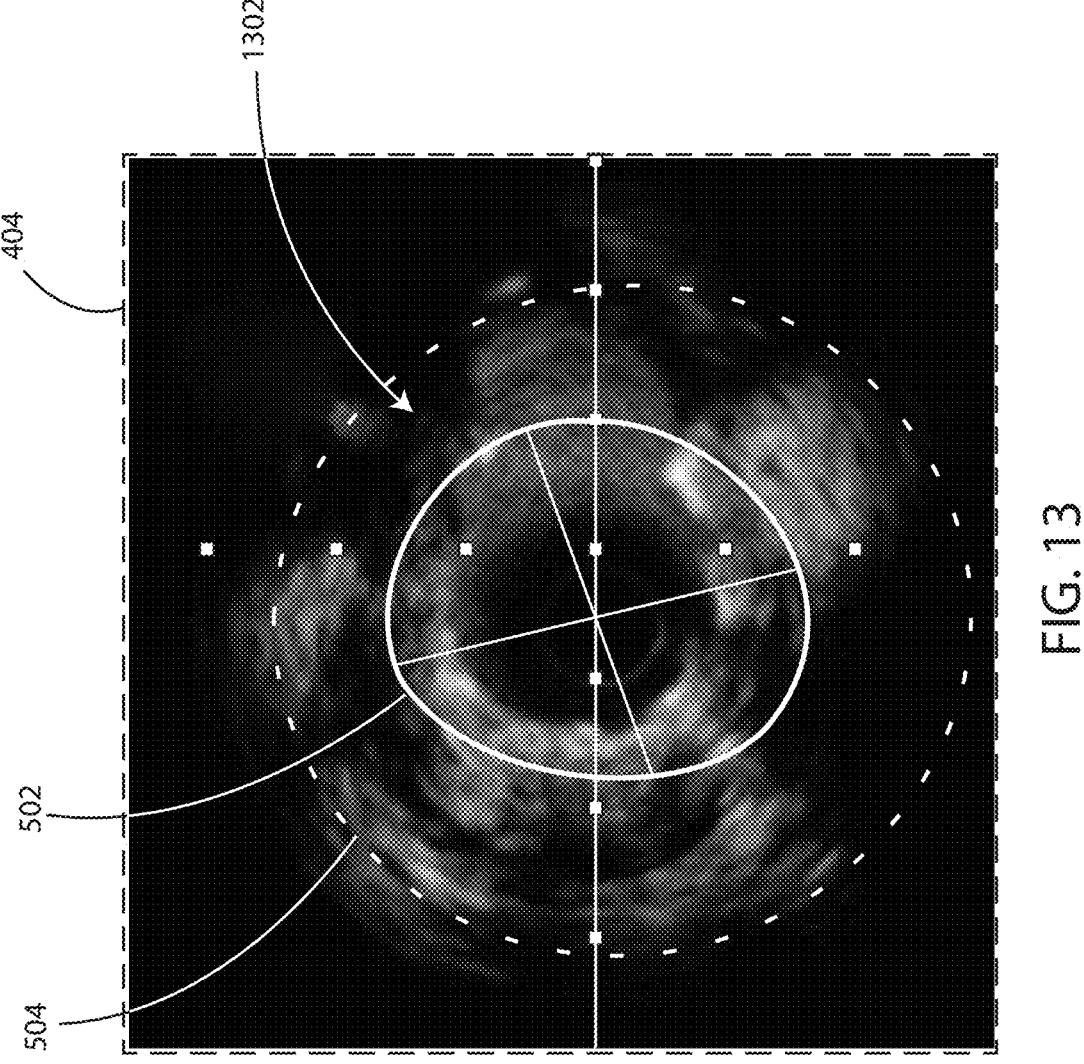
FIG. 13 is a schematic view of components of a display for an intravascular imaging system in accordance with various embodiments herein.

Referring now to FIG. 13, a schematic view is shown of components of a display including a user interface for an intravascular imaging system in accordance with various embodiments herein. In particular, FIG. 13 shows features related to a radial cross section 404 of the vessel being imaged including a drawn lumen border 502 and a drawn vessel border 504. The drawn lumen border 502 and a drawn vessel border 504 are shown to be superimposed over an actual ultrasound image 1302 representing a radial cross-section of a vessel.

In various embodiments, the user interface can be configured to receive user input regarding the displayed graphical features, such as the drawn lumen border and/or the drawn vessel border, from the system user. For example, in some scenarios the system user may view the ultrasound image and disagree with the location of some anatomical features of interest as drawn in by the system. As such, the user interface can be configured to receive user input regarding the user's determination of locations of anatomical features. For example, the user interface can be configured to receive user input regarding at least one of a position of a first vessel border and a position of a second vessel border from the system user. In various embodiments, the intravascular imaging display system can be configured to use the user input as part of a data set for generation of a machine learning model. For example, the user input can be used as training data as part of a supervised machine learning approach to generate an improved model used to automatically determine the location of anatomical features.

Figure 14:
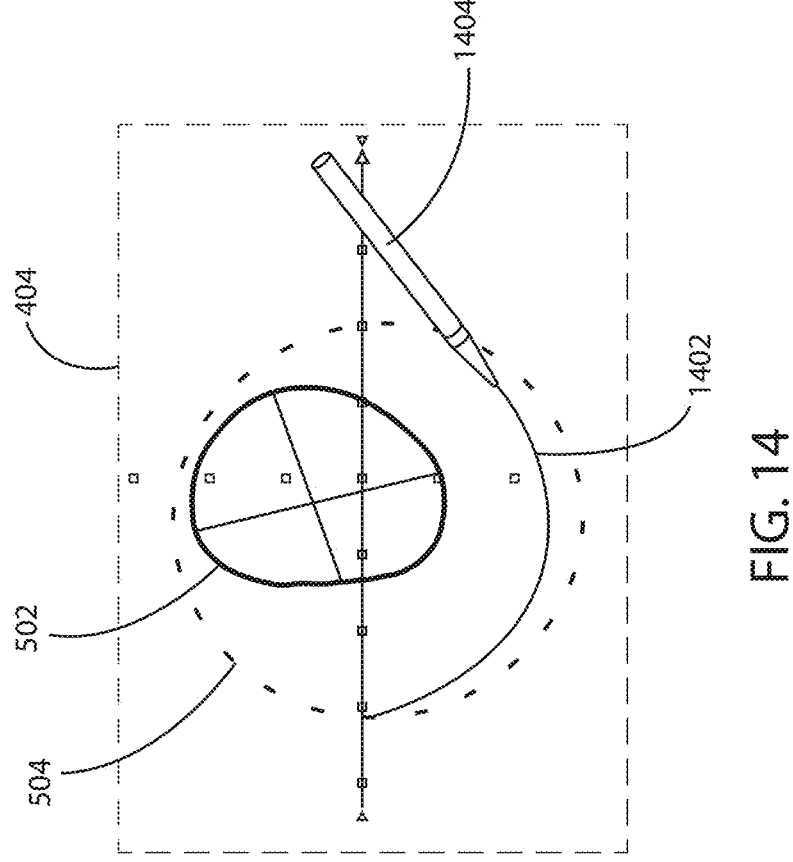
FIG. 14 is a schematic view of components of a display for an intravascular imaging system in accordance with various embodiments herein.

Referring now to FIG. 14, a schematic view of components of a display for an intravascular imaging system is shown in accordance with various embodiments herein. The user interface includes graphical features related to a radial cross section 404 of the vessel being imaged including a drawn lumen border 502 and a drawn vessel border 504. The vessel being imaged can also include a manually drawn border 1402. The manually drawn border 1402 can reflect user input as provided through a user input device 1404 such as a stylus, touch screen input, mouse or other pointer, or the like. Data regarding the manually drawn border 1402 (such as the position of the same) can be saved by the system and/or transmitted to a remote computing resource such as a computing resource in the cloud. In some embodiments, the spatial difference between the drawn vessel border 504 as indicated by the system and the manually drawn border 1402 can be calculated. This difference can be saved and/or transmitted to a remote computing resource.

Figure 15:
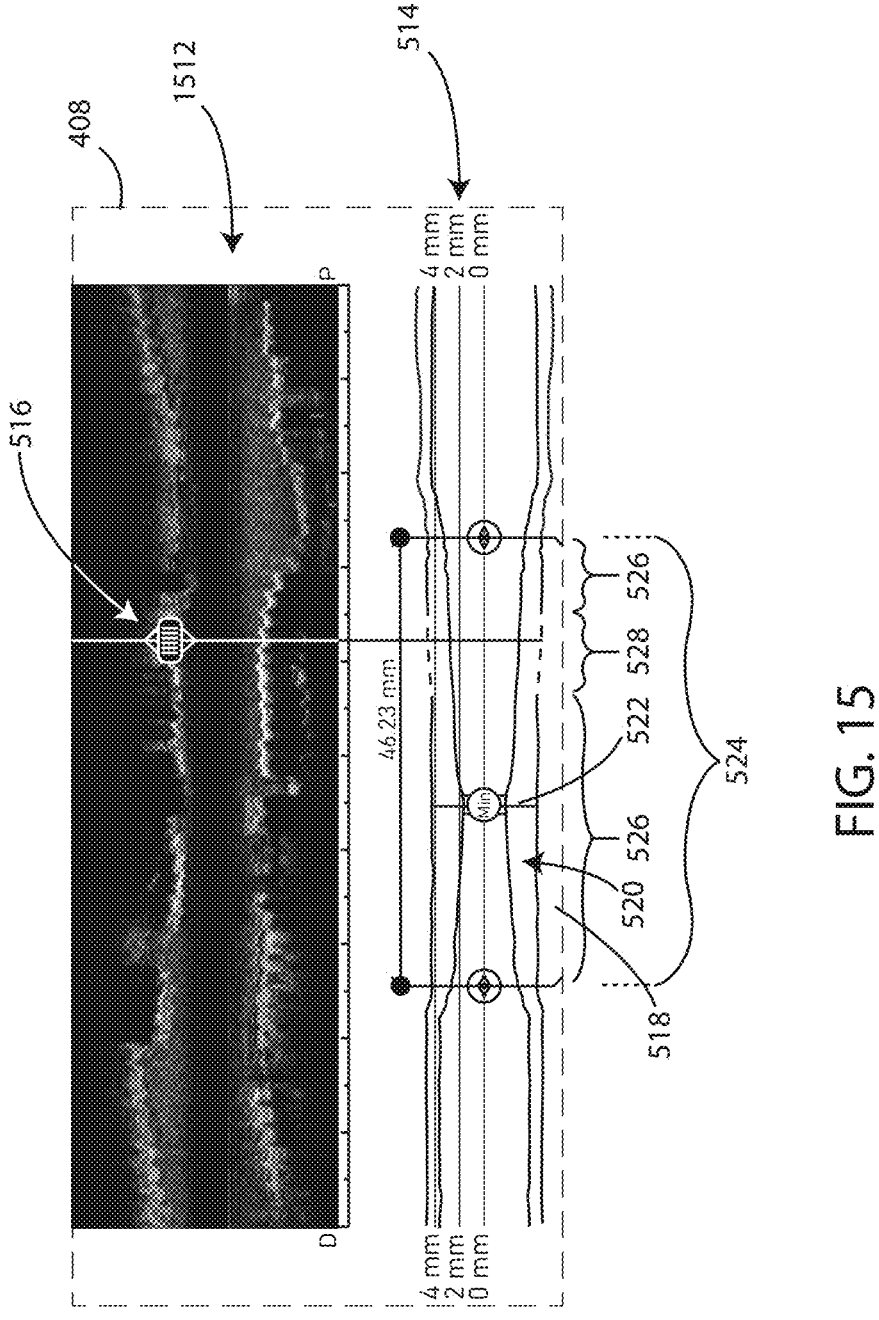
FIG. 15 is a schematic view of components of a display for an intravascular imaging system in accordance with various embodiments herein.

In some embodiments, a composite of actual ultrasound images (frames) representing a longitudinal cross-sectional view of a vessel can be shown within the display. Referring now to FIG. 15, a schematic view is shown of components of a display for an intravascular imaging system in accordance with various embodiments herein. Similar to as described with respect to FIG. 5, FIG. 15 shows graphical components related to a longitudinal cross section 408. In this example, the graphical components related to a longitudinal cross section 408 can include a navigation slider 516 that can be used by the system user to navigate quickly navigate through the image data longitudinally along the length of the imaged vessel. FIG. 15 also shows a longitudinal vessel wall representation 514 including a focus area 524 with a lumen 520 and a vessel wall 518. The vessel wall 518 can include a first vessel wall portion 528 and a second vessel wall portion 526. The first vessel wall portion 528 includes a first lumen border 502. The first vessel wall portion 528 also includes a first vessel border 504. The user interface can also include a marker of the minimum cross-sectional area 522 of the lumen. The first vessel wall portion 528 and the second vessel wall portion 526 can be assigned to represent one or more locations along a vessel wall 518 by a control circuit 106 based on a degree of attenuation of an ultrasound return signal crossing a threshold value. However, FIG. 15 also shows a composite of ultrasound images (frames) 1512 representing a longitudinal cross-sectional view of the vessel being imaged.

Figure 16:
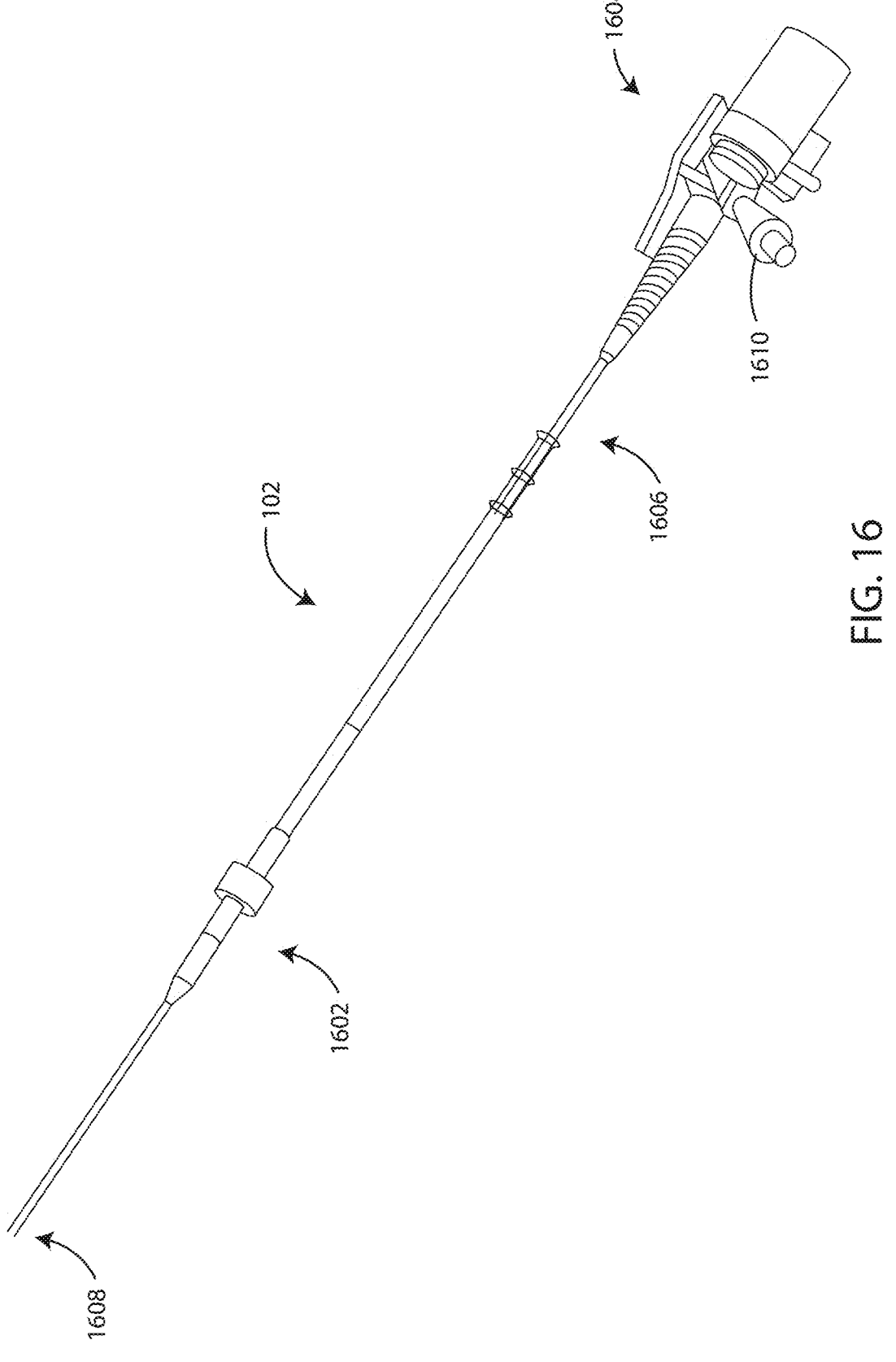
FIG. 16 is a schematic side view of an intravascular imaging catheter of an IVUS imaging system is shown in accordance with various embodiments herein.

Referring now to FIG. 16, a schematic side view is shown of a catheter 102 of an IVUS imaging system is shown in accordance with various embodiments herein. While an IVUS system is shown by way of example, it will be appreciated that the features described herein can also be applied to other intravascular imaging systems. The catheter 102 includes an elongated member 1602 and a hub 1604. The elongated member 1602 includes a proximal end 1606 and a distal end 1608. In FIG. 16, the proximal end 1606 of the elongated member 1602 is coupled to the catheter hub 1604 and the distal end 1608 of the elongated member is configured and arranged for percutaneous insertion into a patient. Optionally, the catheter 102 may define at least one flush port, such as flush port 1610. The flush port 1610 may be defined in the hub 1604. The hub 1604 may be configured and arranged to couple to the control module. In some instances, the elongated member 1602 and the hub 1604 are formed as a unitary body. In other instances, the elongated member 1602 and the catheter hub 1604 are formed separately and subsequently assembled together.

Figure 17:
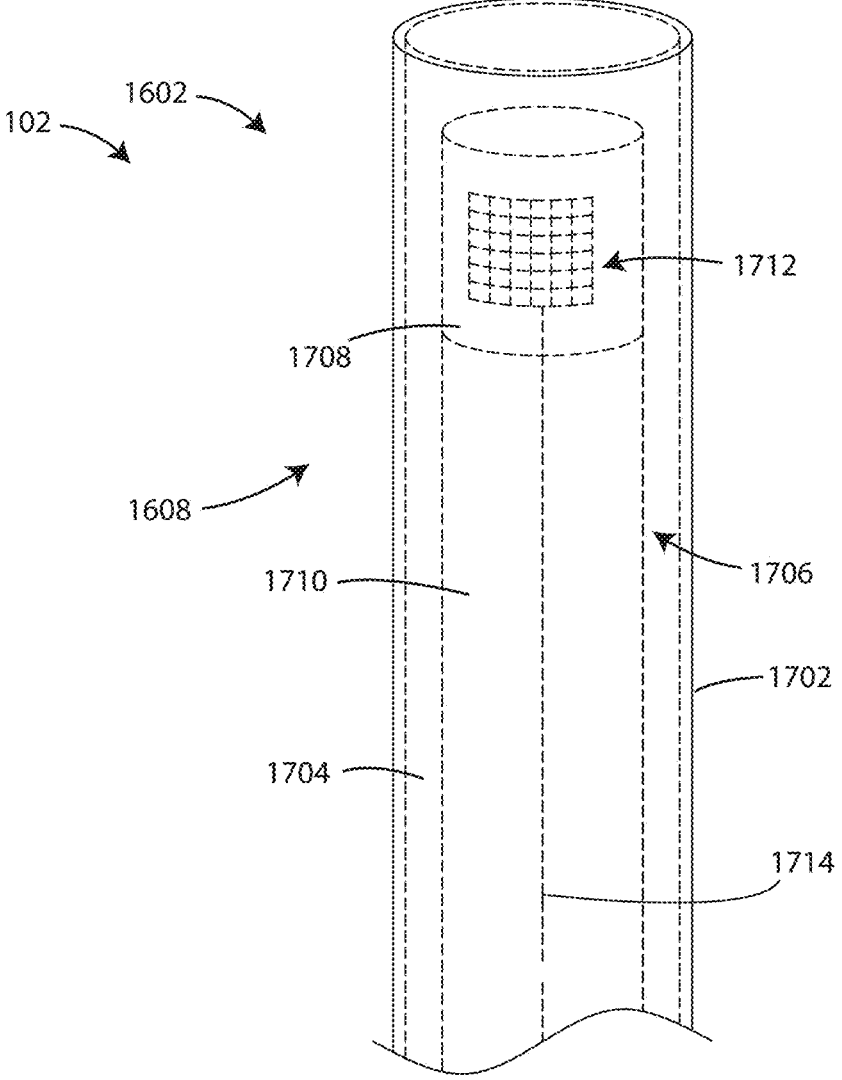
FIG. 17 is a schematic perspective view of the distal end of an elongated member of an intravascular imaging catheter in accordance with various embodiments herein.

Referring now to FIG. 17, a schematic perspective view is shown of the distal end 1608 of the elongated member 1602 of the catheter 102 in accordance with various embodiments herein. The elongated member 1602 includes a sheath 1702 with a longitudinal axis (e.g., a central longitudinal axis extending axially through the center of the sheath 1702 and/or the catheter 102) and a lumen 1704. An imaging core 1706 is disposed in the lumen 1704. The imaging core 1706 includes an imaging device 1708 coupled to a distal end of a driveshaft 1710 that is rotatable either manually or using a computer-controlled drive mechanism. One or more transducers 1712 may be mounted to the imaging device 1708 and employed to transmit and receive acoustic signals. The sheath 1702 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In some instances, for example as shown in FIG. 17, an array of transducers 1712 are mounted to the imaging device 1708. Alternatively, a single transducer may be employed. Any suitable number of transducers 1712 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 1712 are employed, the transducers 1712 can be configured into any suitable arrangement including, for example, an annular arrangement, a rectangular arrangement, or the like.

The one or more transducers 1712 may be formed from materials capable of transforming applied electrical pulses to pressure distortions on the surface of the one or more transducers 1712, and vice versa. Examples of suitable materials include piezoelectric ceramic materials, piezo-composite materials, piezoelectric plastics, barium titanates, lead zirconate titanates, lead metaniobates, polyvinylidene fluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The pressure distortions on the surface of the one or more transducers 1712 form acoustic pulses of a frequency based on the resonant frequencies of the one or more transducers 1712. The resonant frequencies of the one or more transducers 1712 may be affected by the size, shape, and material used to form the one or more transducers 1712. The one or more transducers 1712 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 1712 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 1712 can be used to form a radial cross-sectional image of a surrounding space. Thus, for example, when the one or more transducers 1712 are disposed in the catheter 102 and inserted into a blood vessel of a patient, the one more transducers 1712 may be used to form an image of the walls of the blood vessel and tissue surrounding the blood vessel.

The imaging core 1706 is rotated about the longitudinal axis of the catheter 102. As the imaging core 1706 rotates, the one or more transducers 1712 emit acoustic signals in different radial directions (e.g., along different radial scan lines). For example, the one or more transducers 1712 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module where a processor processes the electrical-signal characteristics to form a displayable image of the imaged region based, at least in part, on a collection of information from each of the acoustic pulses transmitted and the echo pulses received. In some instances, the rotation of the imaging core 1706 is driven by the drive unit 110 disposed in the control module. In alternate embodiments, the one or more transducers 1712 are fixed in place and do not rotate. In which case, the driveshaft 1710 may, instead, rotate a mirror that reflects acoustic signals to and from the fixed one or more transducers 1712.

When the one or more transducers 1712 are rotated about the longitudinal axis of the catheter 102 emitting acoustic pulses, a plurality of images can be formed that collectively form a radial cross-sectional image (e.g., a tomographic image) of a portion of the region surrounding the one or more transducers 1712, such as the walls of a blood vessel of interest and tissue surrounding the blood vessel. The radial cross-sectional image can, optionally, be displayed on one or more display units 114. The imaging core 1706 can be either manually rotated or rotated using a computer-controlled mechanism.

The imaging core 1706 may also move longitudinally along the blood vessel within which the catheter (depicted in FIG. 1) is inserted so that a plurality of cross-sectional images may be formed along a longitudinal length of the blood vessel. During an imaging procedure the one or more transducers 1712 may be retracted (e.g., pulled back) along the longitudinal length of the catheter. The catheter can include at least one telescoping section that can be retracted during pullback of the one or more transducers 1712. In some instances, the drive unit drives the pullback of the imaging core 1706 within the catheter. The drive unit pullback distance of the imaging core can be any suitable distance including, for example, at least 5 cm, 10 cm, 15 cm, 20 cm, 25 cm, or more. The entire catheter can be retracted during an imaging procedure either with or without the imaging core 1706 moving longitudinally independently of the catheter.

A stepper motor may, optionally, be used to pull back the imaging core 1706. The stepper motor can pull back the imaging core 1706 a short distance and stop long enough for the one or more transducers 1712 to capture an image or series of images before pulling back the imaging core 1706 another short distance and again capturing another image or series of images, and so on.

The quality of an image produced at different depths from the one or more transducers 1712 may be affected by one or more factors including, for example, bandwidth, transducer focus, beam pattern, as well as the frequency of the acoustic pulse. The frequency of the acoustic pulse output from the one or more transducers 1712 may also affect the penetration depth of the acoustic pulse output from the one or more transducers 1712. In general, as the frequency of an acoustic pulse is lowered, the depth of the penetration of the acoustic pulse within patient tissue increases. In some instances, the intravascular imaging system 100 operates within a frequency range of 5 MHz to 100 MHz.

One or more conductors 1714 can electrically couple the transducers 1712 to the control module (depicted in FIG. 1). In which case, the one or more conductors 1714 may extend along a longitudinal length of the rotatable driveshaft 1710.

The catheter with one or more transducers 1712 mounted to the distal end 1608 of the imaging core 1708 may be inserted percutaneously into a patient via an accessible blood vessel, such as the femoral artery, femoral vein, or jugular vein, at a site remote from the selected portion of the selected region, such as a blood vessel, to be imaged. The catheter may then be advanced through the blood vessels of the patient to the selected imaging site, such as a portion of a selected blood vessel.

An image or image frame ("frame") can be generated each time one or more acoustic signals are output to surrounding tissue and one or more corresponding echo signals are received by the imager 1708 and transmitted to the processor. Alternatively, an image or image frame can be a composite of scan lines from a full or partial rotation of the imaging core or device. A plurality (e.g., a sequence) of frames may be acquired over time during any type of movement of the imaging device 1708. For example, the frames can be acquired during rotation and pullback of the imaging device 1708 along the target imaging location. It will be understood that frames may be acquired both with or without rotation and with or without pullback of the imaging device 1708. Moreover, it will be understood that frames may be acquired using other types of movement procedures in addition to, or in lieu of, at least one of rotation or pullback of the imaging device 1708.

In some instances, when pullback is performed, the pullback may be at a constant rate, thus providing a tool for potential applications able to compute longitudinal vessel/plaque measurements. In some instances, the imaging device 1708 is pulled back at a constant rate of about 0.3-0.9 mm/s or about 0.5-0.8 mm/s. In some instances, the imaging device 1708 is pulled back at a constant rate of at least 0.3 mm/s. In some instances, the imaging device 1708 is pulled back at a constant rate of at least 0.4 mm/s. In some instances, the imaging device 1708 is pulled back at a constant rate of at least 0.5 mm/s. In some instances, the imaging device 1708 is pulled back at a constant rate of at least 0.6 mm/s. In some instances, the imaging device 1708 is pulled back at a constant rate of at least 0.7 mm/s. In some instances, the imaging device 1708 is pulled back at a constant rate of at least 0.8 mm/s.

In some instances, the one or more acoustic signals are output to surrounding tissue at constant intervals of time. In some instances, the one or more corresponding echo signals are received by the imager 1708 and transmitted to the control circuit 106 (which can include a processor) at constant intervals of time. In some instances, the resulting frames are generated at constant intervals of time.

At least some conventional IVUS imaging systems display only a single (e.g., cross-sectional, longitudinal, or the like) image during, or after, an IVUS procedure, such as a pull-back procedure. It may, however, be useful to concurrently display, in real-time during the IVUS procedure (e.g., a pull-back procedure), at least two images, such as the most recently processed image and a previously obtained image that has some particular or selected image characteristic (e.g., maximum or minimum lumen area or diameter).

Some diagnostic and/or therapeutic interventions may include the analysis of images generated by the IVUS imaging system. This analysis, however, may require a substantial amount of training/experience in order to efficiently interpret the images. Furthermore, due to the frequent presence of speckles on IVUS images, automated analysis and/or evaluation may also be challenging. Disclosed herein are methods for processing and/or analyzing images such as images generated with/by an IVUS imaging system. Such methods may utilize machine learning, artificial intelligence, deep neural networks, and/or the like to improve the processing and/or analysis of images generated with/by an IVUS imaging system.

The processes/methods disclosed herein may include the generation and/or collection of images of a blood vessel (e.g., IVUS images, cross-sectional images, etc. generated via an IVUS pullback procedure). The generated/collected images may be subjected to processing and/or segmentation of the images using deep learning networks (e.g., deep neural networks such as the U-Net deep neural network) to obtain image segmentation for quantitative analysis and image classification for automated identification of lesion type, stent detection, identification of the lumen border, identification of the lumen dimensions, identification of the minimum lumen area (MLA), identification of the media border (e.g., identification of a media border for media within the blood vessel), identification of the media dimensions, identification of the calcification angle/arc, identification of the calcification coverage, identification of the lesion types, combinations thereof, and/or the like. In addition to identifying such border/dimension, the output may be displayed on a display unit in a suitable format (e.g., graphically, numerically, as a real or schematic image, with words or symbols, etc.). In some instances, multiple images of an IVUS pullback or "run" may be analyzed. The output of this run analysis may include a lumen profile (e.g., including, for example, a longitudinal section or "long view"), a vessel profile (e.g., including, for example, a longitudinal section or "long view"), a representation (e.g., visualization or image, numerical visualization, graphical visualization, and/or the like) of the calcification length, the depiction/display of reference frames (e.g., such as the minimal lumen area or "MLA", the minimal stent area or "MSA", or the like), a representation (e.g., visualization or image, numerical visualization, graphical visualization, and/or the like) of side branch location, a representation (e.g., visualization or image, numerical visualization, graphical visualization, and/or the like) of the distance between two frames of interest, a representation (e.g., visualization or image, numerical visualization, graphical visualization, and/or the like) of stent extension, combinations thereof, and/or the like. This may also include analyzing the images with a deep neural network (e.g., such as UNet deep neural network—a convolutional neural network developed for biomedical image segmentation or another neural network) and/or other machine learning and/or artificial intelligence approaches. Other deep learning neural networks that can be applied in some scenarios can include deep belief networks, generative adversarial networks, recurrent neural networks, and other types of convolutional deep neural networks.

Some example IVUS imaging systems that may be used, for example with the embodiments and/or operations herein, include, but are not limited to, those disclosed in, U.S. Pat. Nos. 7,246,959; 7,306,561; and 6,945,938; as well as U.S. Patent Application Publication Nos. US 2006/0100522; US 2006/0106320; US 2006/0173350; US 2006/0253028; US 2007/0016054; US 2007/0038111; and WO2021/062006 all of which are incorporated herein by reference.

Methods

Many different methods are contemplated herein, including, but not limited to, methods of generating images for an intravascular imaging display system, methods of generating or controlling a user interface for an intravascular imaging display system, methods of using an intravascular imaging display system, and the like. Aspects of system/device operation described elsewhere herein can be performed as operations of one or more methods in accordance with various embodiments herein and can be performed with a control circuit or component thereof such as a processor, microcontroller, ASIC, or the like or other hardware components locally or remotely such as in the cloud.

In various embodiments, operations described herein and/or method steps can be performed as part of a computer-implemented method executed by one or more processors of one or more computing devices. In various embodiments, operations described herein and method steps can be implemented as instructions stored on a non-transitory, computerreadable medium that, when executed by one or more processors, cause a system to execute the operations and/or steps.

In an embodiment, a method of providing a display for an intravascular imaging display system is included, the method can include distinguishing between a first vessel wall portion and a second vessel wall portion based on a degree of attenuation of an ultrasound return signal. The method can also include generating a display output including a user interface, wherein the user interface includes a representation of the vessel wall including the first vessel wall portion and the second vessel wall portion. A representation of the first vessel wall portion can be at least partially defined by a first graphic indicator and a representation of the second vessel wall portion can be at least partially defined by a second graphic indicator.

In an embodiment, the first graphic indicator can include a solid line border. In an embodiment, the second graphic indicator can include an interrupted line border. However, many other variations are also contemplated herein including those described elsewhere herein.

In an embodiment of the method, the representation of the vessel wall is displayed as a longitudinal cross-section of the vessel. In an embodiment of the method, the representation of the vessel wall is displayed as a radial cross-section of the vessel. In an embodiment of the method, the representation of the vessel wall is displayed as both a longitudinal cross-section of the vessel and a radial cross-section of the vessel.

In an embodiment of the method, locations of components of the vessel wall representation are determined using a machine learning derived model. In an embodiment of the method, locations of components of the vessel wall representation are determined using a deep learning derived model.

In an embodiment, the method can further include receiving user input regarding the vessel wall representation such as the locations of anatomical features thereof from a system user. In an embodiment, the method can further include receiving user input regarding a vessel border. In an embodiment, the method can further include receiving user input regarding a position of a vessel border from a system user. In an embodiment of the method, the user input can be used as part of a training data set for generation of a machine learning model to determine the locations of anatomical features of interest within ultrasound images.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An intravascular imaging display system comprising:
a control circuit; and
a video output circuit;
wherein the video output circuit is in electronic communication with the control circuit;
wherein the video output circuit is configured to generate a display output including a user interface;
the user interface comprising
graphical elements related to a vessel being imaged, the graphical elements comprising
a first detected feature portion, wherein the first detected feature portion is at least partially defined by a first graphic indicator; and
a second detected feature portion, wherein the second detected feature portion is at least partially defined by a second graphic indicator;
wherein the first graphic indicator is visually distinct from the second graphic indicator;
wherein the first detected feature portion and the second detected feature portion are assigned to represent a first vessel wall portion and a second vessel wall portion along a vessel wall by the control circuit based on a degree of attenuation of an ultrasound return signal crossing a threshold value, respectively; and
wherein the first graphical indicator and the second graphical indicator represent different degrees of positional accuracy or confidence based on the degree of attenuation.

2. The intravascular imaging display system of claim 1, the first graphic indicator comprising a solid line border.

3. The intravascular imaging display system of claim 1, the second graphic indicator comprising an interrupted line border.

4. The intravascular imaging display system of claim 1, wherein the graphical elements are related to a longitudinal cross-section of the vessel.

5. The intravascular imaging display system of claim 1, wherein the graphical elements are related to a radial cross-section of the vessel.

6. The intravascular imaging display system of claim 1, the first detected feature portion comprising:

a representation of a first lumen border; and
a representation of a first vessel border;
the second detected feature portion comprising
a representation of a second lumen border; and
a representation of a second vessel border.

7. The intravascular imaging display system of claim 6, wherein the position of the representations of the first vessel border, the second vessel border, the first lumen border, and the second lumen border are determined using a machine learning derived model.

8. The intravascular imaging display system of claim 6, wherein the position of the representations of the first vessel border, the second vessel border, the first lumen border, and the second lumen border are determined using a deep learning derived model.

9. The intravascular imaging display system of claim 1, the user interface comprising one or more numerical parameters related to the vessel being imaged, wherein the one or more numerical parameters include a typographic feature to indicate whether they relate to the first detected feature portion or the second detected feature portion.

10. The intravascular imaging display system of claim 1, wherein the user interface is configured to receive user input regarding the position of the graphical elements from a system user.

11. The intravascular imaging display system of claim 1, wherein the user interface is configured to receive user input regarding at least one of a position of a representation of a first vessel border and a position of a representation of a second vessel border from a system user.

12. The intravascular imaging display system of claim 11, wherein the intravascular imaging display system is configured to use the user input as part of a data set for generation of a machine learning model.

13. The intravascular imaging display system of claim 1, wherein the first detected feature portion comprises one or more discrete portions separated by one or more discrete portions of the second detected feature portion.

14. A method of providing a display for an intravascular imaging display system comprising:
distinguishing between a first vessel wall portion and a second vessel wall portion based on a degree of attenuation of an ultrasound return signal; and
generating a display output including a user interface;
wherein the user interface includes graphical elements related to a vessel being imaged including a first detected feature portion corresponding to the first vessel wall portion and a second detected feature portion corresponding to the second vessel wall portion;
wherein the first detected feature portion is at least partially defined by a first graphic indicator and the second detected feature portion is at least partially defined by a second graphic indicator;
wherein the first graphic indicator is visually distinct from the second graphic indicator; and
wherein the first graphic indicator and the second graphic indicator represent different degrees of positional accuracy or confidence based on the degree of attenuation.

15. The method of claim 14, the first graphic indicator comprising a solid line border and the second graphic indicator comprising an interrupted line border.

16. The method of claim 14, further comprising determining positions of the graphical elements related to a vessel being imaged using a machine learning derived model.

17. The method of claim 14, further comprising determining positions of the graphical elements related to a vessel being imaged using a deep learning derived model.

18. The method of claim 14, further comprising receiving user input regarding the graphical elements related to a vessel being imaged from a system user.

19. The method of claim 18, further comprising receiving user input regarding a position of a vessel border from a system user.

20. The method of claim 19, further comprising using the user input as part of a training data set for generation of a machine learning model.

* * * * *